(12) United States Patent
Zasloff et al.

(10) Patent No.: US 8,987,236 B2
(45) Date of Patent: Mar. 24, 2015

(54) THERAPEUTIC USES FOR AN AMINOSTEROL COMPOUND

(71) Applicant: Ohr Pharmaceutical, Inc., New York, NY (US)

(72) Inventors: Michael Zasloff, Merion, PA (US); Jon Williams, Dana Point, CA (US); William Kinney, Doylestown, PA (US); Mark Anderson, Eagleville, PA (US); Michael McLane, Lansdale, PA (US)

(73) Assignee: Ohr Pharmaceutical, Inc., New York, NY (US)

( * ) Notice: Subject to any disclaimer, the term of this patent is extended or adjusted under 35 U.S.C. 154(b) by 0 days.

(21) Appl. No.: 13/673,500

(22) Filed: Nov. 9, 2012

(65) Prior Publication Data

US 2013/0281419 A1    Oct. 24, 2013

Related U.S. Application Data

(63) Continuation of application No. 12/041,440, filed on Mar. 3, 2008, now abandoned, which is a continuation of application No. 09/885,247, filed on Jul. 13, 2000, now Pat. No. 7,410,959.

(51) Int. Cl.
*A01N 45/00*    (2006.01)
*A61K 31/56*    (2006.01)
*A61K 31/575*    (2006.01)
*C07J 41/00*    (2006.01)

(52) U.S. Cl.
CPC ........... *A61K 31/575* (2013.01); *C07J 41/0055* (2013.01)
USPC .......................................... 514/169; 514/182

(58) Field of Classification Search
CPC ......................... A61K 31/575; C07J 41/0055
USPC .................................................. 514/182, 169
See application file for complete search history.

(56) References Cited

U.S. PATENT DOCUMENTS

| | | | |
|---|---|---|---|
| 3,370,070 A | 2/1968 | Klimstra et al. | |
| 5,004,737 A | 4/1991 | Kim et al. | |
| 5,192,756 A | 3/1993 | Zasloff et al. | |
| 5,721,226 A | 2/1998 | Frye et al. | |
| 5,733,899 A | 3/1998 | Frye et al. | |
| 5,763,430 A * | 6/1998 | Zasloff | 514/169 |
| 5,792,635 A | 8/1998 | Zasloff | |
| 5,795,885 A * | 8/1998 | Zasloff et al. | 514/182 |
| 5,840,936 A * | 11/1998 | Zasloff et al. | 552/521 |
| 5,842,740 A | 12/1998 | Lefranc | |
| 5,847,172 A | 12/1998 | Zasloff et al. | |
| 6,143,738 A * | 11/2000 | Zasloff | 514/181 |
| 7,410,959 B1 * | 8/2008 | Zasloff et al. | 514/182 |
| 7,728,157 B2 * | 6/2010 | Kinney et al. | 552/521 |

FOREIGN PATENT DOCUMENTS

| | | |
|---|---|---|
| FR | 2361899 A1 | 3/1978 |
| GB | 1565351 A | 4/1980 |
| WO | 94/20520 A | 9/1994 |
| WO | 95/24415 A | 9/1995 |
| WO | 96/08270 A | 3/1996 |
| WO | 96/40151 A1 | 12/1996 |
| WO | 96/40728 A2 | 12/1996 |
| WO | 97/44044 A1 | 11/1997 |
| WO | 98/24800 A | 12/1997 |
| WO | 98/19682 A1 | 5/1998 |

OTHER PUBLICATIONS

Beers, "The Merck Manual of Diagnosis and Therapy," 17th Ed, 1654-1656 (1999).
Zasloff et al., "A spermine-coupled cholesterol metabolite from the shark with potent appetite suppressant and antidiabetic properties," International Journal of Obesity, 25: 689-697 (2001).
Zasloff et al., "A centrally acting cholesterol metabolite with potent appetite suppressant and antidiabetic properties," Pediatric Research, 47: 142A (2002).
Jones et al., "The synthesis and characterization of analogs of the antimicrobial compound squalamine: 6beta-hydroxy-3-aminosterols synthesized from hyodeoxycholic acid," Steroids, 61: 565-571 (1996).
Wehrli et al., "Structure of the novel steroidal antibiotic squalamine determined by two-dimensional NMR spectroscopy," Steroids, 58: 370-378 (1993).

* cited by examiner

*Primary Examiner* — Yong Chong
(74) *Attorney, Agent, or Firm* — Morgan, Lewis & Bockius LLP

(57) ABSTRACT

A pharmaceutical composition includes, as an active ingredient, a compound according to formula 1436 as shown in FIG. 1, or a pharmaceutically acceptable salt thereof, and a pharmaceutically acceptable carrier or excipient. Various pharmaceutical products may be produced including this pharmaceutical composition. Such pharmaceutical products may be used for the treatment of obesity or diabetes. Methods for using the pharmaceutical compositions also are described. In these methods, various diseases are treated or other body functions are activated or inhibited by administering an effective amount of the pharmaceutical composition. For example, diabetes and obesity may be treated by administering an effective amount of the pharmaceutical compositions. Weight gain and growth factor production can be inhibited by administering an effective amount of these pharmaceutical compositions. Appetite can be suppressed by administering an effective amount of the pharmaceutical compositions, and a diuretic effect can be produced.

2 Claims, 18 Drawing Sheets

THERAPEUTIC USES FOR AN AMINOSTEROL COMPOUND

RELATED APPLICATION DATA

The present application is a continuation application of U.S. application Ser. No. 12/041,440 (filed Mar. 8, 2008) which is a continuation of U.S. application Ser. No. 09/885,247 (filed Jul. 13, 2000) which are hereby incorporated by reference in their entireties.

BACKGROUND OF THE INVENTION

I. Information Relating to Previous Patents and Applications

Several aminosterol compositions have been isolated from the liver and stomach of the dogfish shark, *Squalus acanthias*. One important aminosterol, squalamine, is the subject of U.S. Pat. No. 5,192,756 to Zasloff, et al., which patent is entirely incorporated herein by reference. That patent describes the antibiotic properties of squalamine. Since the discovery of squalamine, several interesting properties of this compound have been discovered. For example, as described in U.S. Pat. Nos. 5,733,899 and 5,721,226, squalamine may function as an antiangiogenic agent. These patents are entirely incorporated herein by reference. Additional uses of squalamine (e.g., as an NHE3 inhibiting agent and as an agent for inhibiting the growth of endothelial cells) are disclosed in U.S. Pat. No. 5,792,635, U.S. Pat. No. 6,147,060 and WO 00/015176. These patents and application also are entirely incorporated herein by reference.

Methods for synthesizing squalamine have been devised, such as the methods described in WO 98/24800 (published Jun. 10, 1998) and in U.S. Patent Appl. No. 60/032,378. This PCT publication and the U.S. patent application are entirely incorporated herein by reference. The PCT application relates to U.S. Pat. No. 6,262,283, which patent also is entirely incorporated herein by reference. Additionally, U.S. Pat. No. 5,792,635 also discloses squalamine isolation and synthesis techniques.

Stemming from the discovery of squalamine, other aminosterols have been discovered in the dogfish shark liver and stomach and have been investigated. One important aminosterol that has been isolated and identified has the structure shown in FIG. 1. In this application, the compound having the structure shown in FIG. 1 will be referred to as "compound 1436" or simply "1436." This compound has the general molecular formula $C_{37}H_{72}N_4O_5S$ and a calculated molecular weight of 684.53017.

Compound 1436 previously has been described in U.S. Pat. Nos. 5,795,885, 5,763,430, and 5,847,172. Each of these U.S. patents is entirely incorporated herein by reference. These U.S. patents describe the structure of compound 1436 and other aminosterols, as well as processes for synthesizing and isolating compound 1436 and related aminosterols. For example, compound 1436 may be prepared from squalamine as starting material. Additional methods for synthesizing compound 1436 (as well as squalamine) are described in U.S. Provisional Patent Appl. No. 60/032,378, filed Dec. 6, 1996, which application is entirely incorporated herein by reference.

As further described in these patents and patent applications, compound 1436 has a variety of interesting properties. For example, compound 1436 has been found to be capable of inhibiting mitogen-induced mouse, dog or human T-lymphocyte proliferation, as well as being capable of inhibiting the proliferation of a variety of other cells and tissues.

II. Information Relating to this Application

Compound 1436 and other aminosterol compounds isolated from the dogfish shark liver and stomach have been found to possess interesting antibiotic and anti-proliferative properties with respect to a variety of cells and tissues. These interesting properties of compound 1436 have prompted applicants to conduct further investigation into the uses and properties of this compound.

In addition to treating various ailments and diseases, such as viral based ailments and diseases, cancers, and arthritis, compound 1436 has been found to have other favorable properties and effects. As one specific example, applicants have found that compound 1436 may be used to reduce weight gain in mammals and in a mouse model of type II diabetes to prevent weight gain and to maintain blood glucose at normal levels. The weight gain of the animals in these studies was controlled due to reduction of net food consumption and they were apparently healthy, viable animals.

SUMMARY OF THE INVENTION

This invention relates to a pharmaceutical composition, including a compound according to formula 1436 as shown in FIG. 1, or a pharmaceutically acceptable salt thereof (as an active ingredient), and a pharmaceutically acceptable carrier or excipient. The invention further relates to pharmaceutical products including the pharmaceutical composition described above. Such pharmaceutical products may be provided for the treatment of obesity and diabetes.

In another aspect of this invention it was determined that extended treatment of mice with the compound 1436 not only produced a inhibition of weight gain but also caused a reduction of serum cholesterol levels. Therefore one use for compound 1436 is for the reduction of serum cholesterol and the treatment of atherosclerosis.

In a further embodiment of the invention it was determined that analogues of the compound 1436 were also active in the prevention of weight gain in mice and it was found that the compounds were covered by the following generic formula:

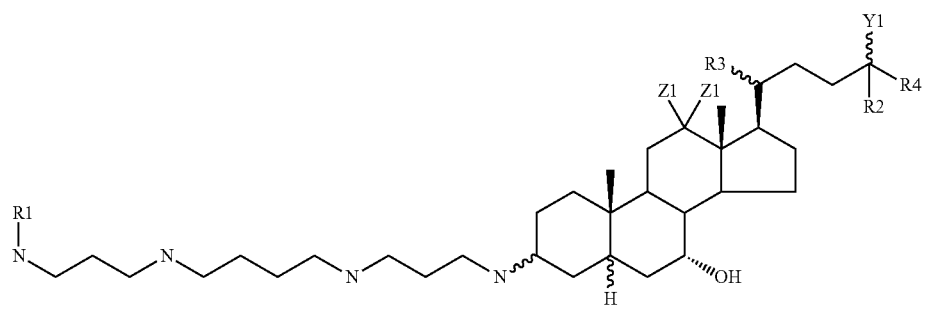

R1=H or C1-C6 alkyl; R2=H or C1-C3 alkyl-X Where X=—H, —OH, —Cl, —Br, —I or —F;
R3=H or C1-C3 alkyl; R4=H or C1-C3 alkyl; Y1=—CO$_2$H, —NH—SO2CF$_3$, —SO3H, —PO3H2, —OSO3H, —CF3 or —F; Z1=H or OH

BRIEF DESCRIPTION OF THE DRAWINGS

These and other advantageous aspects of the invention will be evident from the following detailed description, which should be considered in conjunction with the attached drawings, wherein.

DETAILED DESCRIPTION OF THE INVENTION

As described above, compound 1436 has been discovered in and isolated from the liver and stomach of the dogfish shark. Compound 1436 has been shown to have an effect on weight gain, and specifically in the control of weight gain in the diabetic mouse (db/db). In addition it has been shown to control blood glucose and cholesterol in this mouse and therefore should be useful for the treatment of diabetes and atherosclerosis.

Figure 15A:
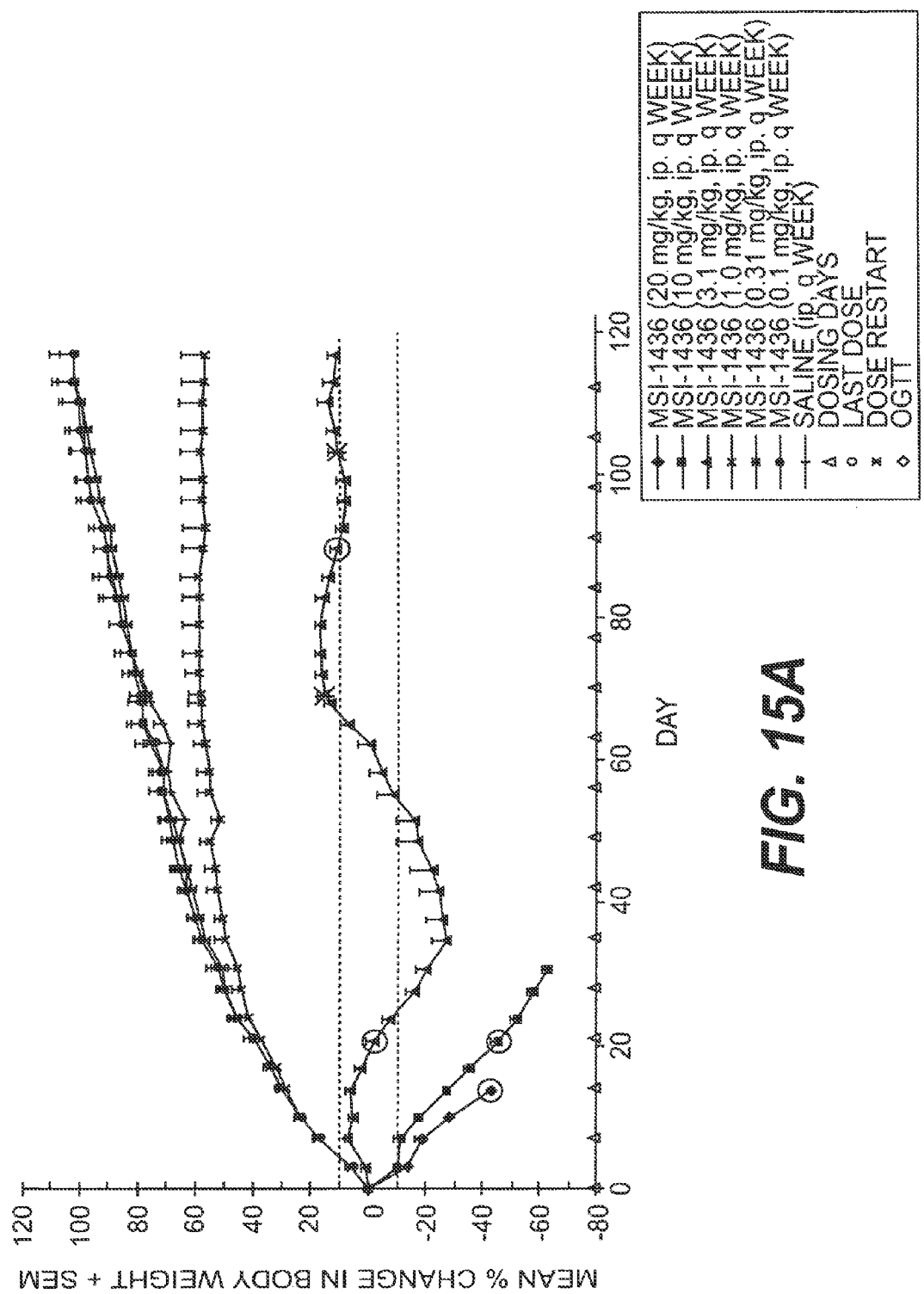
FIG. 15A shows the effect of long term dosing of MSI-1436 as it relates to change in body weight.
Figure 15B:
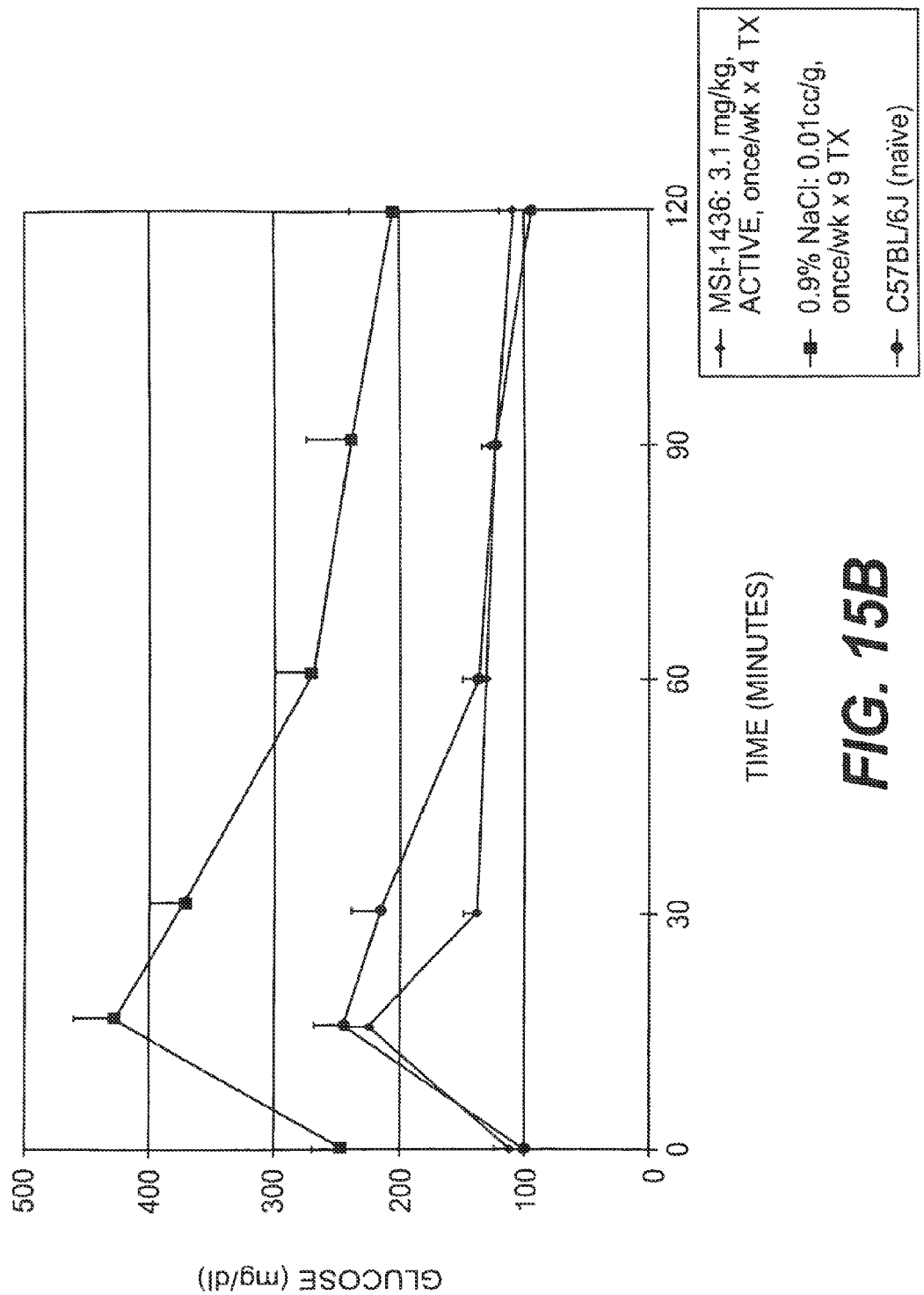
FIG. 15B shows the effect of dosing of MSI-1436 and vehicles as it relates to change in glucose levels.
Figure 15C:
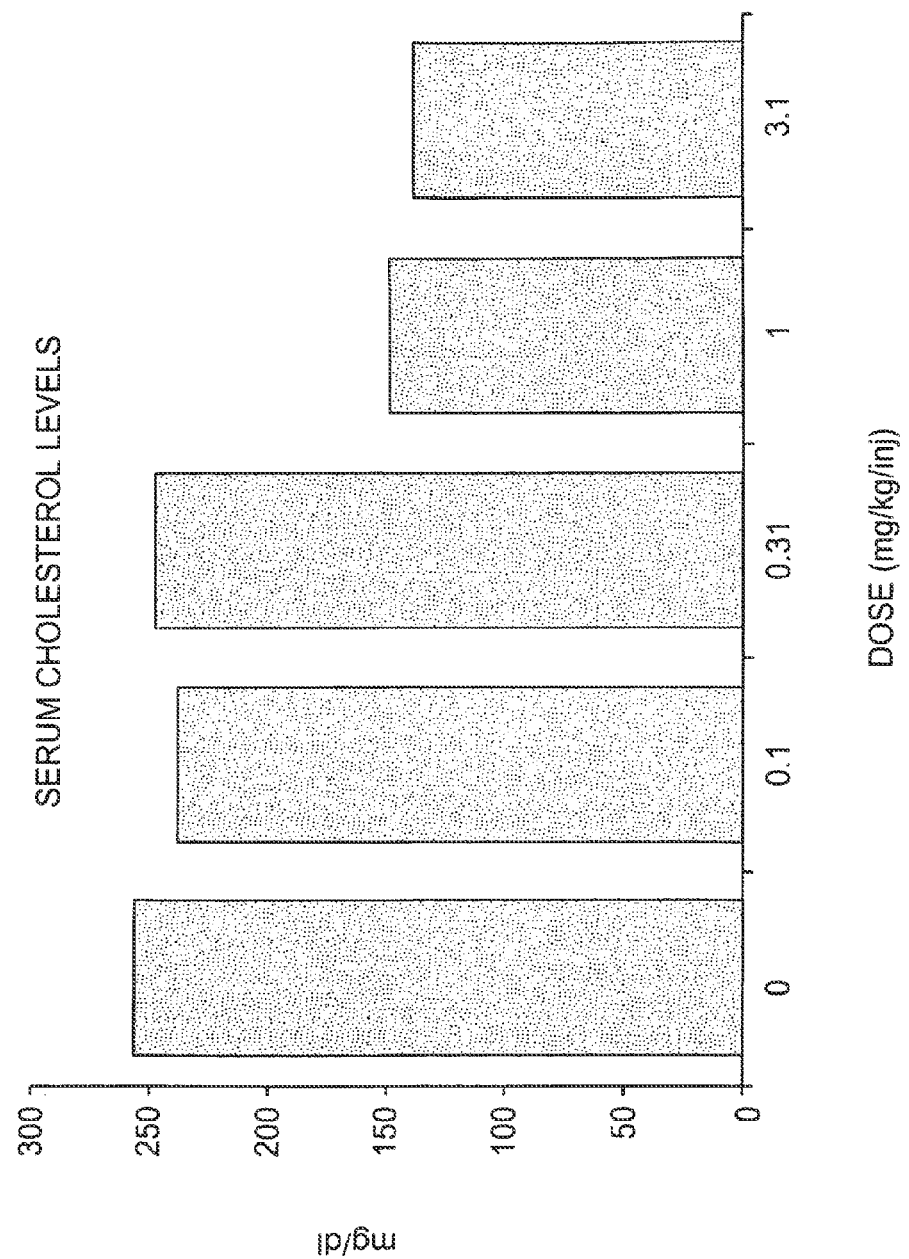
FIG. 15 C compares serum cholesterol levels to various dosing amounts.

To determine the long-term effects of MSI-1436 on the metabolic status of genetically obese mice, ob/ob animals were treated once weekly for 4 months (FIG. 15). MSI-1436 produces a dose dependent reduction in weight gain. Animals receiving 10 or 20 mg/kg/wk lose excessive weight and grow emaciated and moribund within several weeks (FIG. 15). However, safely managed weight control (i.e., no deaths) was possible over a four-month period using an intermittent dosing regimen (FIG. 15 A, 3.1 mg kg/week cohort). When weight fell to about 10% above starting weight, MSI-1436 dosing was stopped, permitting a continued but limited decline in weight; as feeding increased, and weight recovered, dosing resumed. Ob/ob mice eventually develop diabetes, possibly because of fat accumulation within pancreatic islet cells (Chen G, Koyama K, Yuan X, Lee Y, Zhou Y-T, O'Doherty R, Newgard C B, Unger R H. Disappearance of body fat in normal rats induced by adenovirus-mediated leptin gene therapy. Proc. Natl. Acad. Sci. USA 1996; 93: 14795-14799 and Shimabukuro M, Koyama K, Chen G, Wang M-Y, Trieu F, Lee Y, Newgard C B, Unger R H. Direct antidiabetic effect of leptin through triglyceride depletion of tissues. Proc. Natl. Acad. Sci. USA 1997; 94: 4637-4641). Animals were evaluated about 40 days after treatment ceased (day 63). Mice receiving 3.1 mg/kg/week were within 10% above their starting weight, while untreated controls had gained 70%. An oral glucose tolerance test revealed a normal metabolic response in the MSI-1436 treated group, in contrast to the diabetic pattern in the vehicle-treated cohort (FIG. 15 B). At 120 days, after dosing had resumed, serum cholesterol was normalized in animals with controlled weight gain (1.0 and 3.1 mg/kg/week) regardless of their absolute weight (FIG. 15 C)

This invention further relates to various methods for using the pharmaceutical compositions in accordance with the invention. In the methods according to the invention, various diseases or symptoms of diseases or ailments are treated by administering an effective amount of the above-described pharmaceutical composition. "Treat," "treated," or "treating," as used in this application may mean complete elimination of the disease, ailment, or symptoms, or it may mean reducing, suppressing, or ameliorating the severity of the disease, ailment, or symptoms. As examples, certain body functions may be inhibited or enhanced by administering an effective amount of the above-described pharmaceutical compositions. In this manner, weight gain and growth factor production can be inhibited, or a diuretic effect can be produced by administering an effective amount of the pharmaceutical compositions in accordance with the invention. In a further embodiment of the invention compound 1436 can be used to treat type II diabetes where it can be used to prevent excessive weight gain and to control blood glucose levels.

This invention will be described below in terms of various specific examples and preferred embodiments. These examples and embodiments should be considered to be illustrative of the invention, and not as limiting the same.

Example 1

Body Weight Effect of Compound 1436

Tests were conducted on compound 1436 to determine the effect of its administration on the body weight of mammals.

Figure 1:
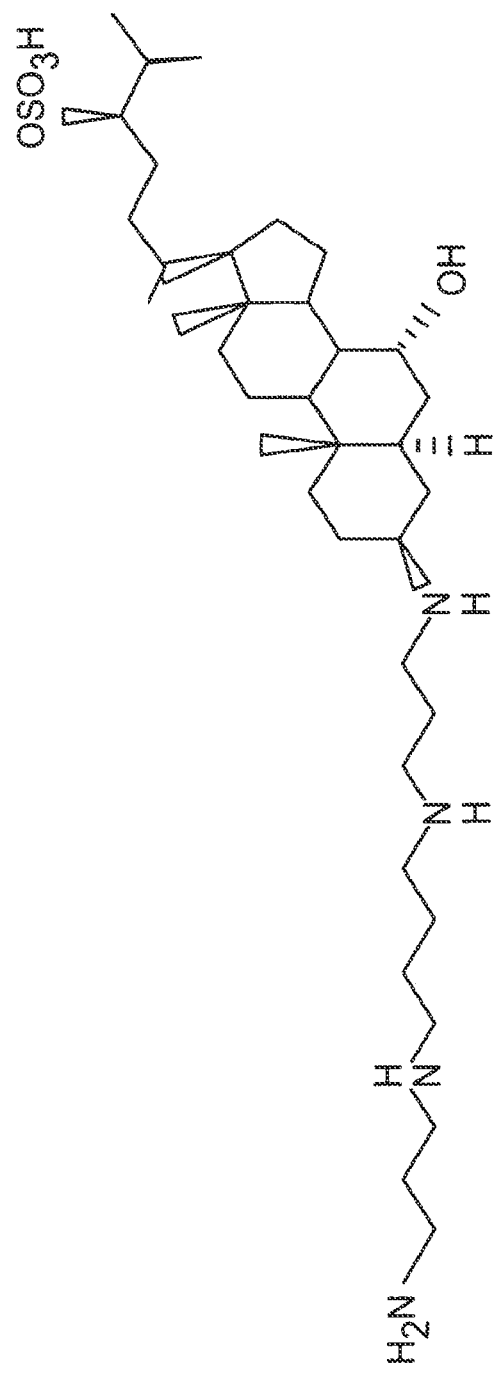
FIG. 1 illustrates the molecular structure of aminosterol 1436.
Figure 2:
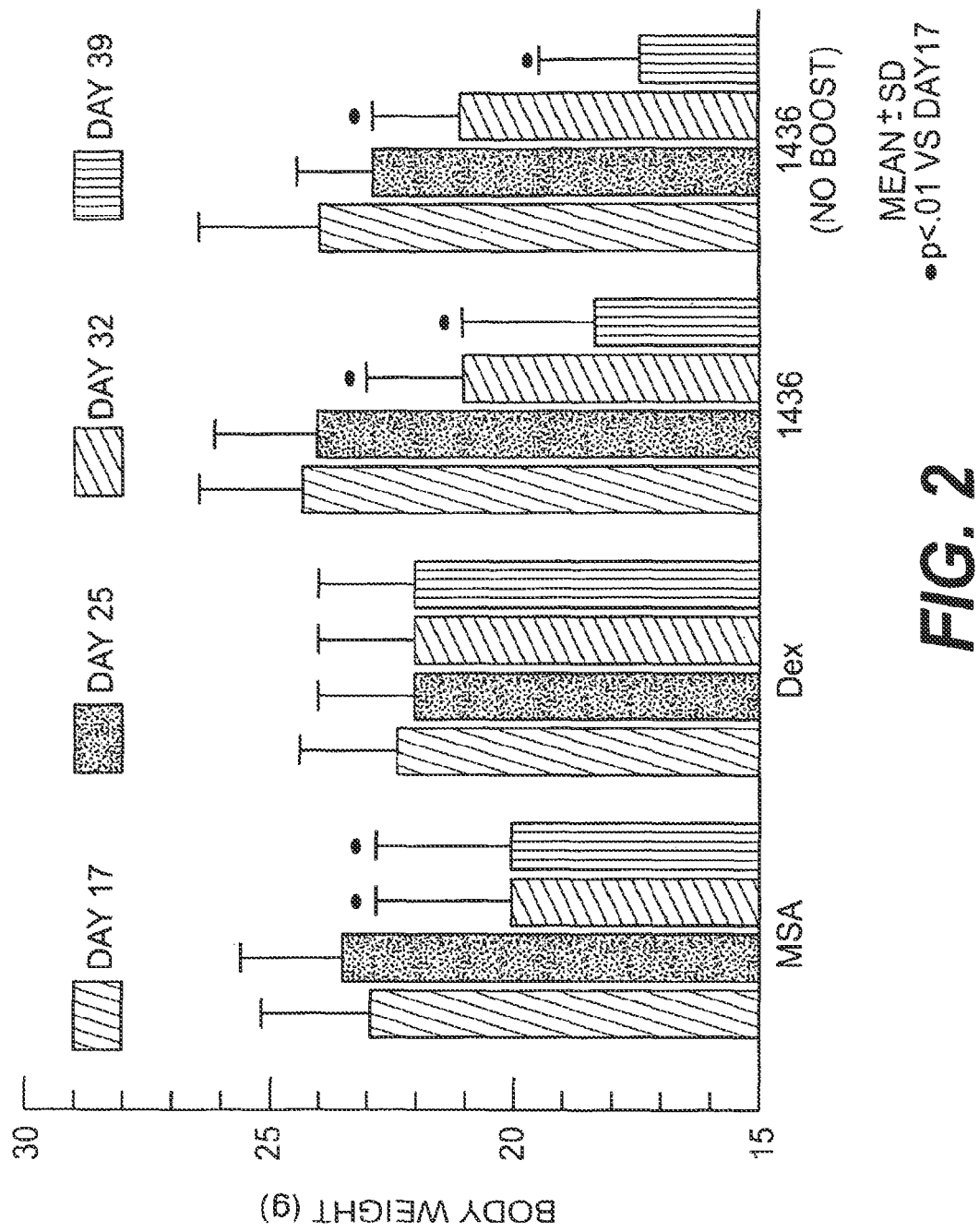
FIG. 2 shows the effect of 1436 on mouse body weight in one study.

An animal model for testing the effectiveness of a compound against arthritis is the bovine type II Collagen Induced Arthritis Model in mice. Six to eight week old mice (male DBA/1LacJ from Jackson Labs) were separated into groups of 10. On Day 0, these mice were immunized subcutaneously with 100 µg of bovine articular cartilage-derived type II collagen in an adjuvant system (RIBI Immunochem.). A booster injection of collagen in RIBI adjuvant was given on Day 21. Compound 1436 was dissolved in sterile, endotoxin-screened dH$_2$O and administered subcutaneously at 200 µg/mouse (10 mg/kg). Dosing with 1436 was continued every fourth day (10 mg/kg) for the duration of the study. An additional group of immunized mice (including 5 mice) was treated in this manner for the purpose of observing the weight-modulating effect of compound 1436. This additional group of 1436 treated mice, did not receive a collagen-booster at Day 21. Like the other group of 1436 treated mice, these mice received their first 1436 dose on Day 17. The mice were weighed approximately weekly on the days indicated in FIG. 2.

Between Day 25 and Day 32, mice in the mouse serum albumin/PBS control group lost about 15% of their body weight, coinciding with the onset and progression of arthritis. See FIG. 2. A similar weight loss was observed in the 1436 treated mice, irrespective of whether the mice received the collagen booster injection at Day 21, and despite the fact that the 1436 treated mice were relatively disease free. While the body weight of the mouse serum albumen/PBS mice remained relatively constant after Day 32, the body weights of the 1436 treated mice (with and without the collagen booster) continued to decline through Day 39. Thus, this study indicates that 1436 may be useful to regulate weight gain. The Dex treated mice showed a stable weight pattern over the entire course of the study period.

In the Collagen Induced Arthritis Model described above, two of the five mice in the additional 1436 control group developed mild arthritis (clinical score of 2) despite having received no collagen booster immunization at Day 21. It was noted, however, that these mice received the priming collagen immunization at Day 0. This priming collagen injection is sufficient to induce arthritis in some animals.

Figure 3:
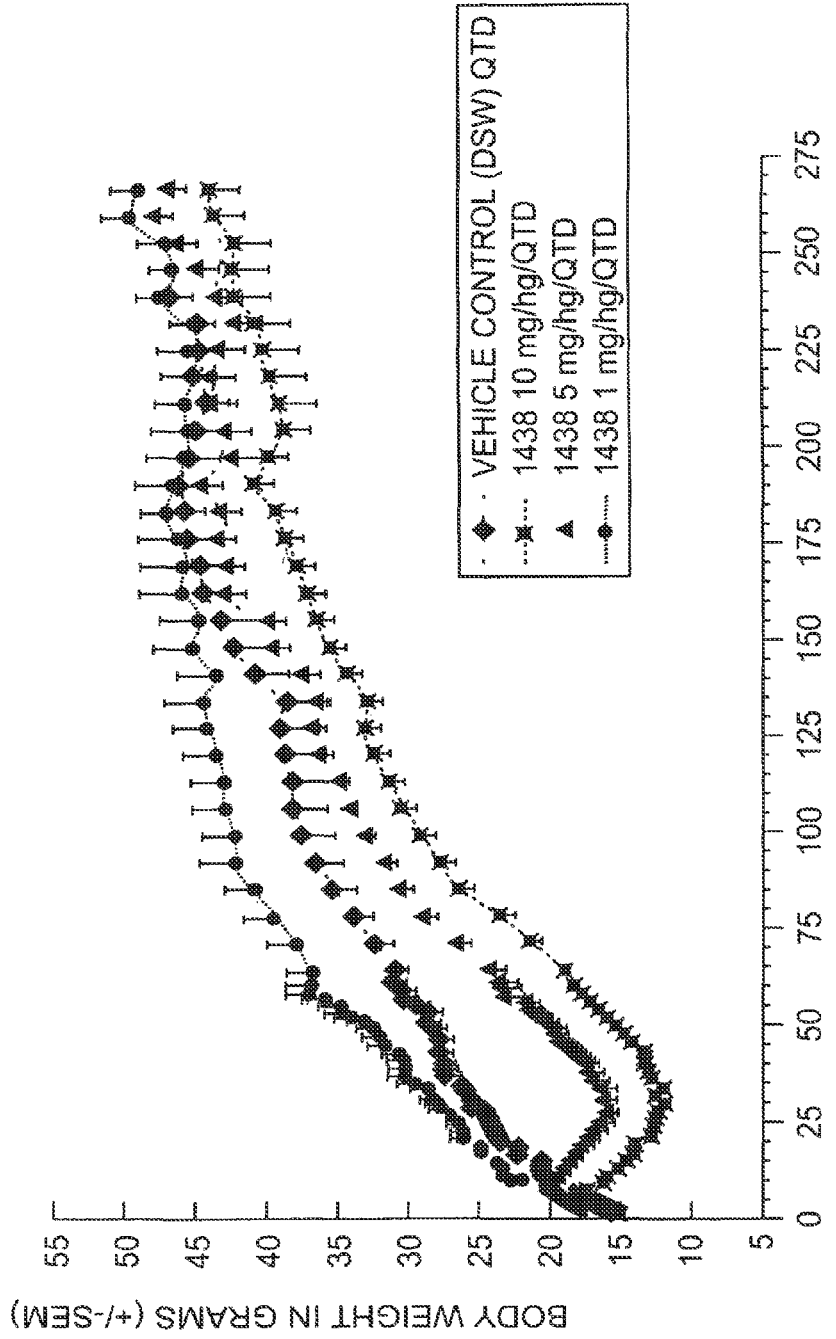
FIG. 3 shows the effect of 1436 on the body weight of mice in a dose response study.

Additional testing was performed to demonstrate the effect of compound 1436 on the body weight of mice. The dosage effect of compound 1436 was tested in one experiment. As illustrated in FIG. 3, compound 1436 was administered subcutaneously into BDF1 male mice in dosages of 1, 5 and 10 mg 1436/kg body weight every third day ("QTD") from Day 1 to Day 22. The control vehicle and the 1436 administration vehicle in this experiment was 5% Dex in water. At 5 and 10 mg/kg 1436, weight gain was suppressed in these groups, and in fact, significant weight loss was experienced. Note the surprising decrease in the body weight of the mice treated with these doses of compound 1436. While these 1436 treated animals experienced a significant weight loss, however, they did not slow down and become lethargic. Rather, they were normally active and apparently healthy. 1 mg/kg 1436 did not appear to have a significant effect on the body weight of the mice in that group. Notably, after the 1436 treatment was stopped (at Day 22), weight gain returned in the animals treated with the 5 and 10 mg 1436/kg body weight doses. Eventually, after 1436 treatment was discontinued, the body weight of the animals in these groups reached the level of the animals in the other groups.

Figure 4:
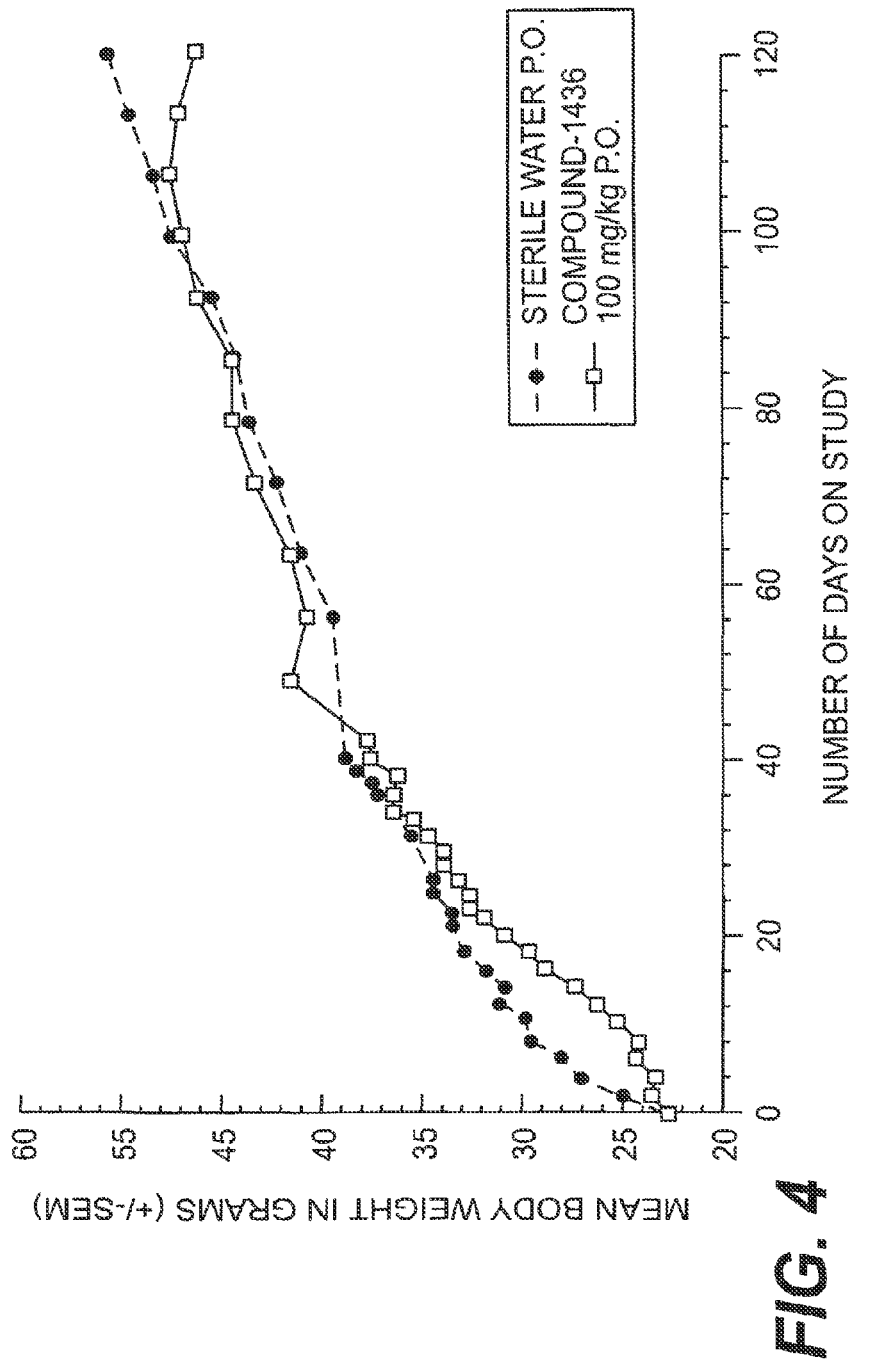
FIG. 4 shows the effect of oral dosing of 1436 on the body weight of mice.

For oral dosing of compound 1436, as shown in FIG. 4, about 60 mg/kg active agent induced a weight suppression effect, which was most obvious on day 10 of the study. In this experiment, the CD-1 male mice were dosed orally with 60 mg/kg active once every third day (QTD) on days 0, 3 and 6, with a dosage volume of 0.01 ml/g. Note that 100 mg/kg 1436 is approximately equivalent to 60 mg/kg active. Again, after 1436 treatment was stopped, the body weight of the 1436 treated animals returned to the level of the animals in the control group.

Figure 5:
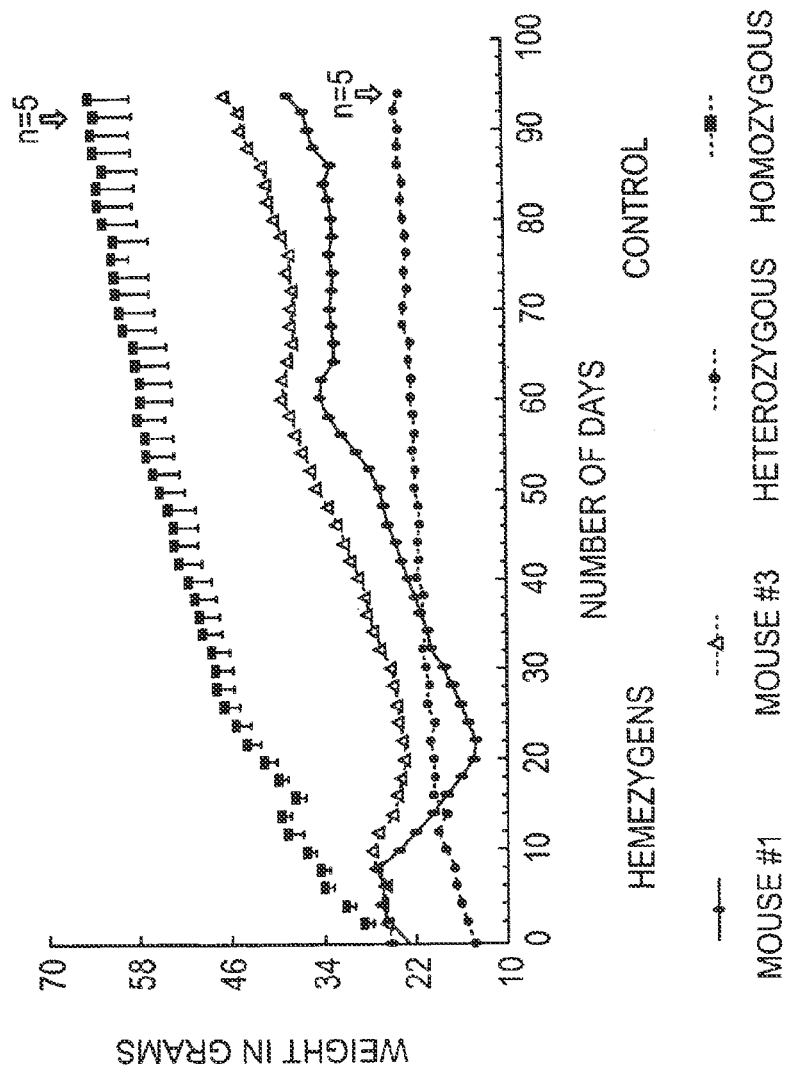
FIG. 5 shows the effect of 1436 on the body weight of obese mice (OB/OB)
Figure 6:
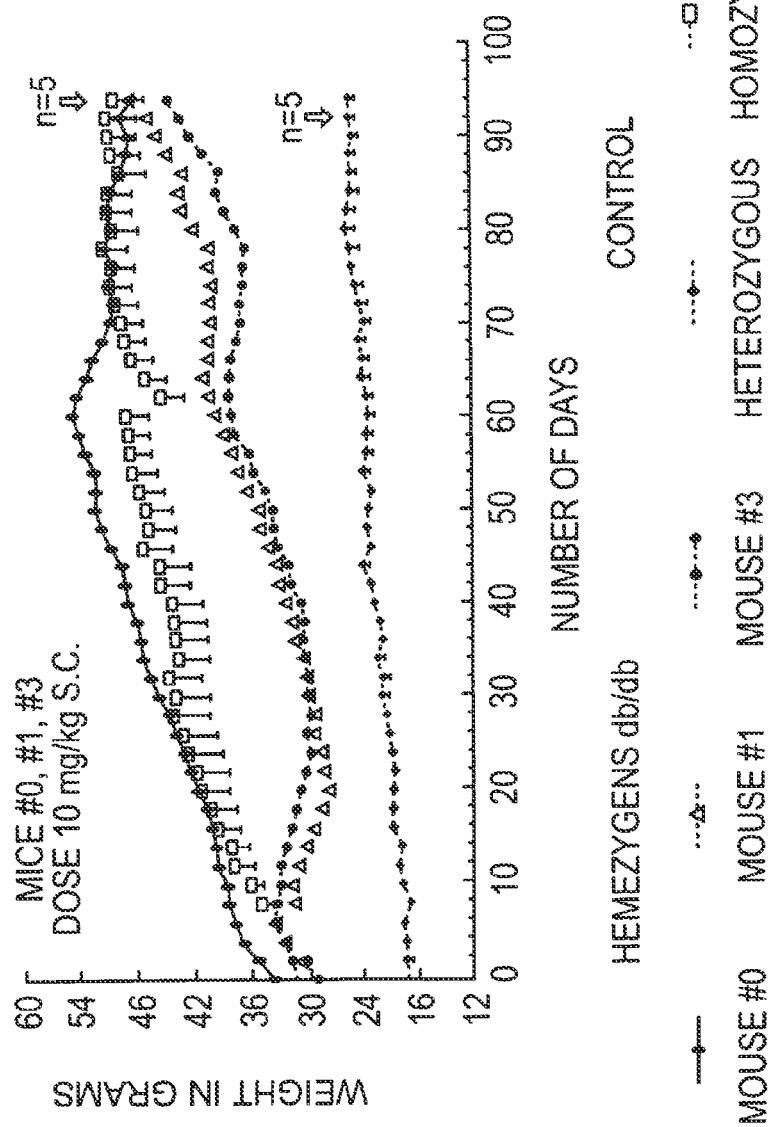
FIG. 6 shows the effect of 1436 on the body weight of diabetic mice (db/db)

In another experiment, genetically obese mice (OB/OB) and diabetic (db/db) mice were treated with compound 1436 to determine the effect on their body weight. Both homozygous (n=5) and heterozygous (n=5) control mice for both OB/OB and db/db mice were treated with sterile $H_2O$ (vehicle). The test results are illustrated in FIGS. 5 and 6. Weight loss and weight control were achieved for the 1436 treated mice. FIGS. 5 and 6 show the effects of compound 1436 (administered s.c. at a dose of 10 mg/kg on days 0, 3 and 6 and 60) on weight in OB/OB and db/db mice, respectively. In FIGS. 5 and 6, "OB/OB" and "db/db" relate to the leptin/leptin receptor.

Figure 7:
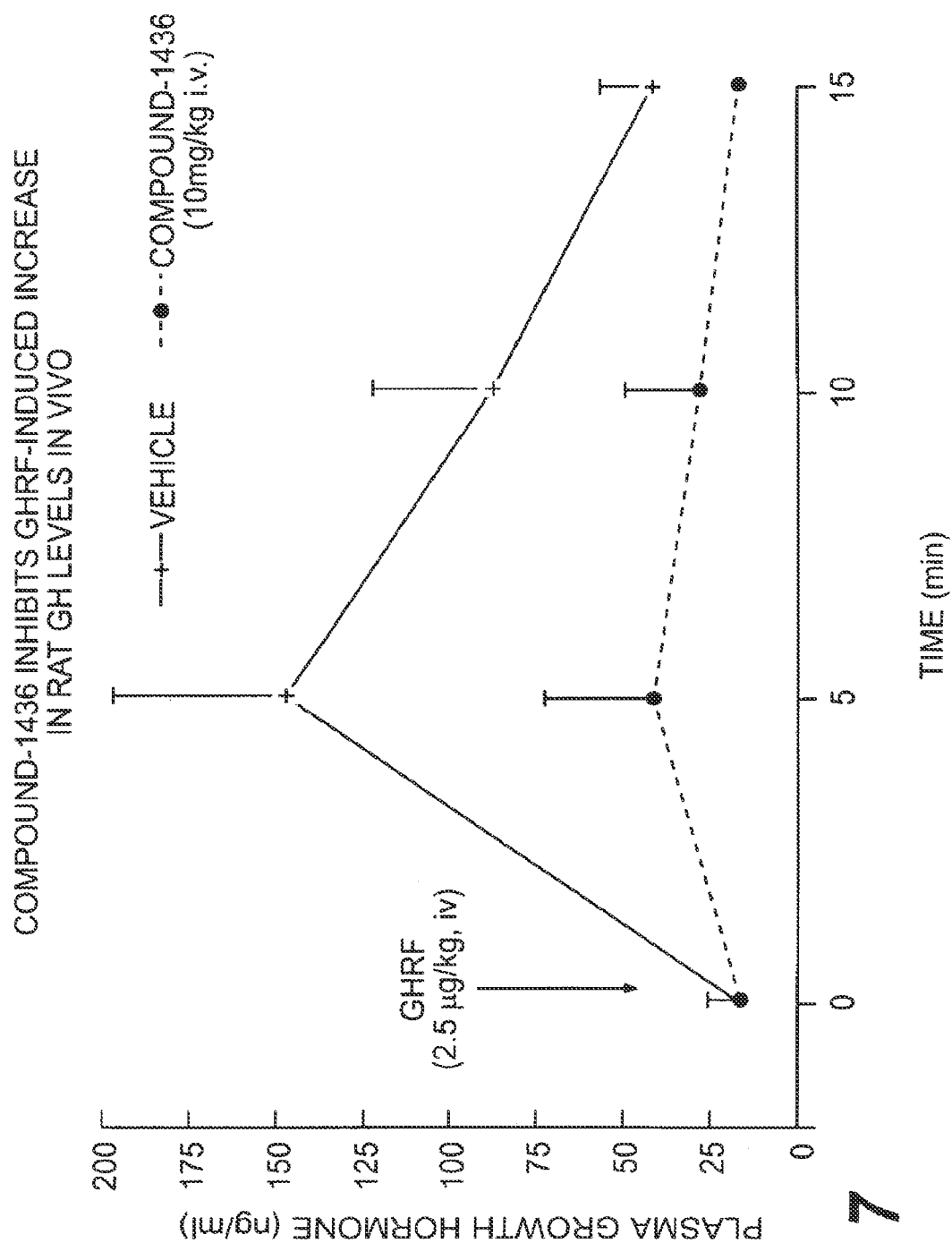
FIG. 7 shows that 1436 inhibits the action of growth hormone releasing factor (GHRF)

The body weight suppression effect of compound 1436 may be the result of suppression of growth factor production and/or growth factor release in the treated animals. To test this possibility, the effect of compound 1436 on release of growth hormone during a GHRF stimulatory test was studied. Compound 1436 or saline (vehicle) was administered at 10 mg/kg i.v. to rats 30 minutes prior to a growth hormone releasing factor (GHRF) challenge (2.5 μg GHRF/kg, i.v. at t=0), and the plasma growth hormone output was measured. Blood samples were taken at t=0, 5, 10 and 15 minutes. As illustrated in FIG. 7, compound 1436 was found to inhibit growth hormone secretion in rats during a GHRF provocation test. In this test, the GHRF is added in this system to induce an increase in growth hormone release.

Figure 8:
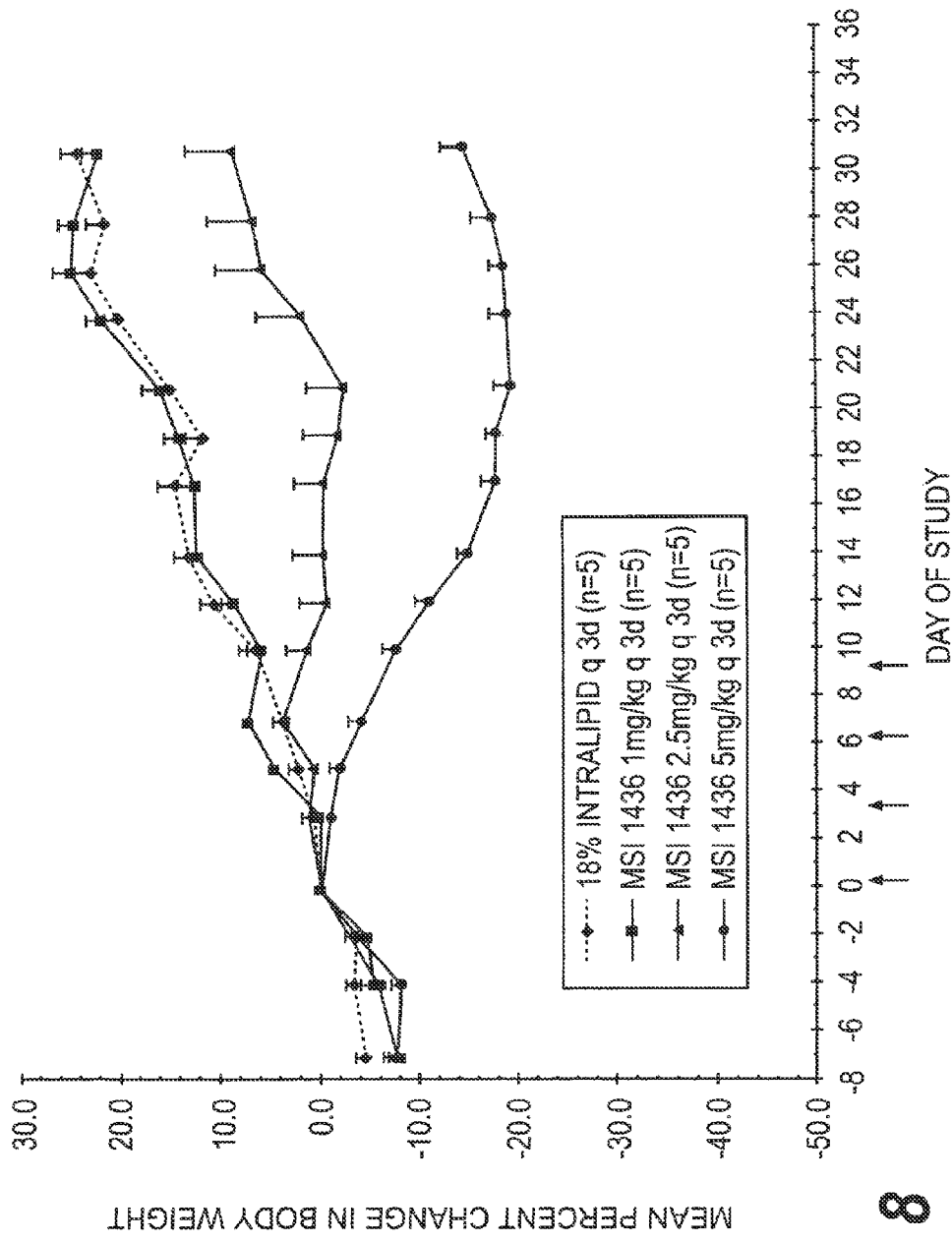
FIG. 8 shows the effect of 1436 on body weight in DBA/2J mice.
Figure 9:
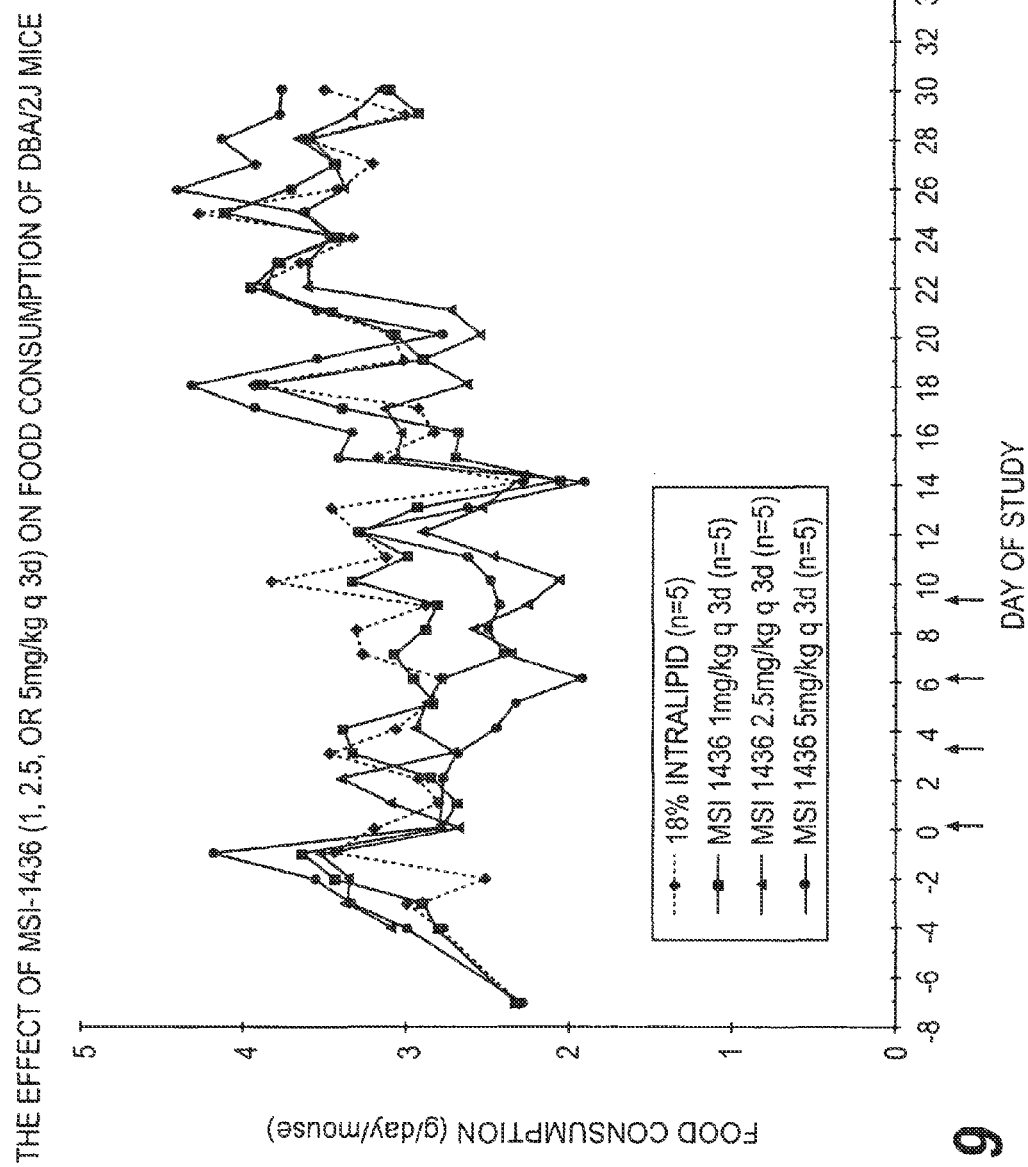
FIG. 9 shows the effect of 1436 on food consumption in DBA/2J mice.
Figure 10:
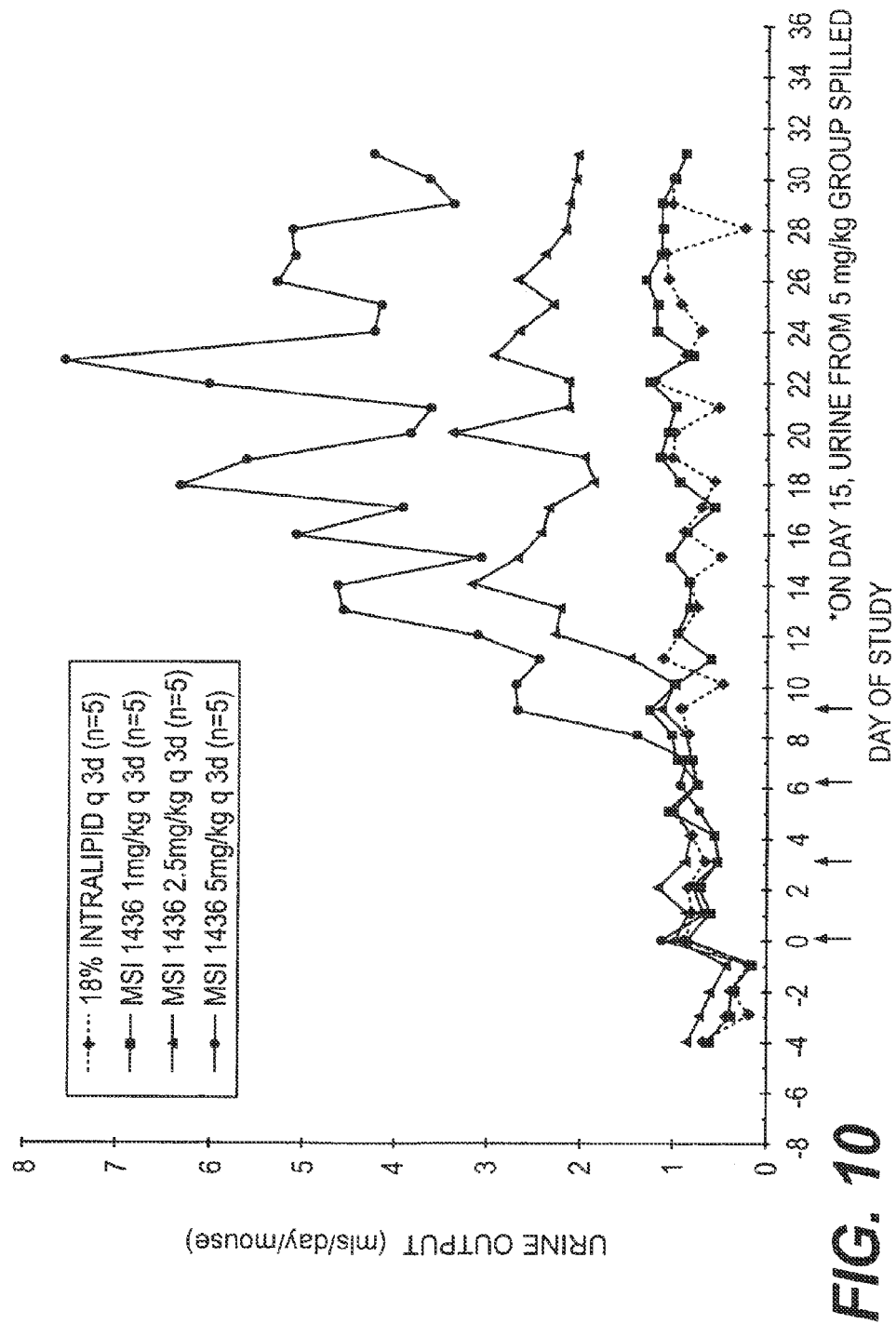
FIG. 10 shows the effect of 1436 on urine output in DBA/2J mice.
Figure 11:
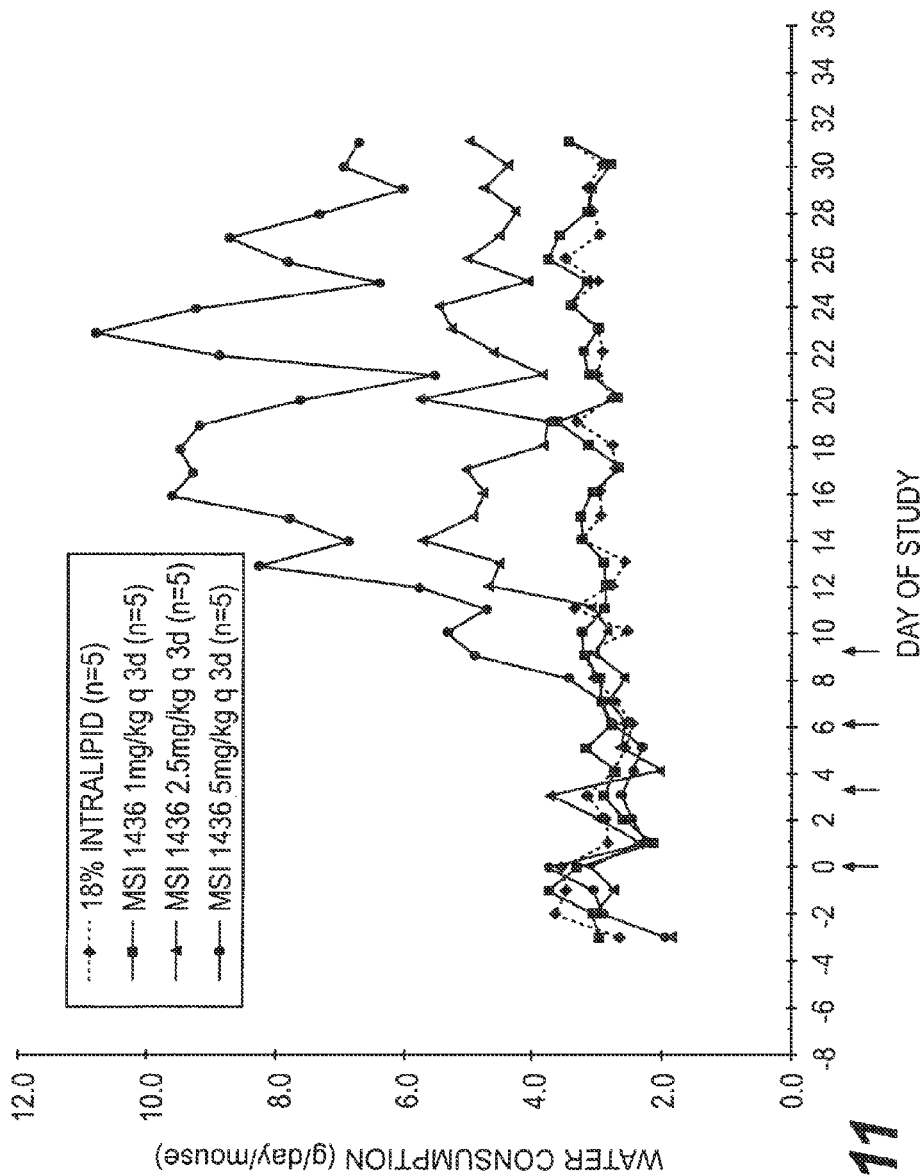
FIG. 11 shows the effect of 1436 on water consumption in DBA/2J mice.

To determine the roles of food and water consumption as well as urine output of compound 1436 on body weight suppression, 20 DBA/2J mice were randomly assigned to one of four groups (5 mice/group) that received either vehicle or compound 1436 at 1, 2.5, or 5 mg active/kg (i.p. every third day ("q 3d") for 4 dosings (i.e., dosed on Days 0, 3, 6 and 9)). Using metabolic cages for accurate measurements, group food consumption, group water consumption, and group urine output were measured daily, and individual body weight were monitored three times per week. FIG. 8 shows a dose-dependent change in body weight. FIG. 9 shows that food consumption of the group receiving compound 1436 at 5 mg/kg was lower than the other groups from Day 3 through Day 7 and lower than vehicle or low dose 1436 from Day 7 through 13. The mid-dose 1436 group had lower food consumption than control or low dose on Days 7 through 14. These reductions in food consumption preceded body weight loss by a few days; the lag would be consistent with a depletion of endogenous fuel storage (fat, glycogen, etc.). FIGS. 10 and 11 show a dose-dependent increase in urine output and water consumption that temporarily aligns with reductions in body weight. Water balance in the body is composed of intake via ingestion and formation of metabolic water and output is via urine, feces and insensible loss (perspiration, respiration). This study only measured water ingested and urine output so the animals may be in a negative water balance, even though water consumption was in excess of urine output. This study suggests that both food consumption as well as a diuresis (negative water balance) may contribute to the suppression of body weight.

Figure 12:
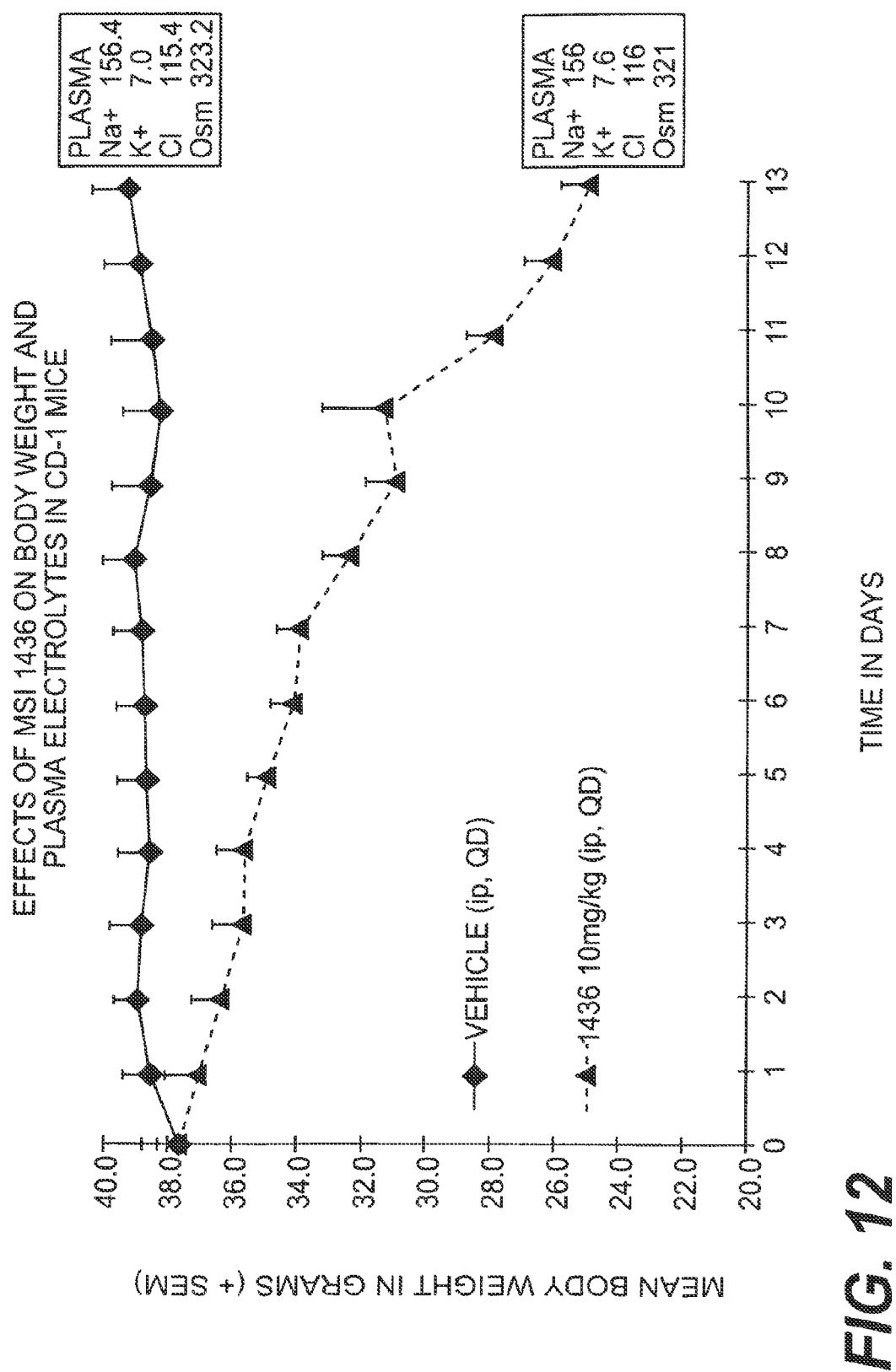
FIG. 12 shows the effect of 1436 on plasma levels of electrolytes and osmolality.

In a separate arm of the study, 10 CD-1 mice (5 mice/group) were randomly assigned to receive either compound 1436 or vehicle as control administered intraperitoneally once per day, every day ("QD") for 13 days (Days 0 to 12). Body weights were monitored daily, and blood samples were obtained on Day 13 (one day post-last administration). Plasma levels of electrolytes (in mEq) and osmolality (in mOsm) were measured. The results in FIG. 12 show that compound 1436 caused weight loss without changing the isotonicity or electrolyte levels of plasma compared to vehicle control mice.

Example 2

Effect of Compound 1436 on Serum Glucose in db/db Mice

Age matched animals (4 females/group) were treated with MSI-1436, 10 mg/kg via the i.p. route every 3 days for a total of 4 doses. Animals were provided food and water ad lib. At day 0, db/db (untreated), db/db (treated), and db/+ (untreated) cohorts weighed 28.1±2.2, 30.8±.1.3 and 17.8±0.9 gms, respectively. At day 20, 7 hours after the last feeding, blood was drawn and glucose determined using a standard clinical glucose meter. Animals were sacrificed and the body composition of the carcasses was determined by published methods (Pellymounter, M. A., M. J. Cullen, M. B. Baker, R. Hecht, D. Winters, T. Boone, and F. Collins. 1995. Effects of the obese gene product on body weight regulation in ob/ob mice. Science 269: 540-543). Over the 20 day period of the study, the weight of untreated homozygotes increased from about 28 to 39 grams. Treated animals dropped from about 31 to 20 grams, losing significant fat and water stores as well as a small but significant fraction of lean mass (Table 1). Treated homozygotes retained more fat than a comparable group of phenotypically normal (but untreated) db/+ heterozygotes (Table 1). Note that the severe hyperglycemia of the db/db homozygote was corrected, reduced from 465.0 mg/dl to 53.5 mg/dl (Table 1).

TABLE 1

Effects of MSI-1436 on body composition and serum glucose in obese mice

| Mice | Treatment | Body Composition | | | | | | Serum |
|---|---|---|---|---|---|---|---|---|
| | | Water | | Fat | | Lean mass | | |
| | | g | % | g | % | g | % | Glucose |
| db/db | saline | 12.6 | 32.4 | 20.7 | 52.8 | 5.8 | 14.8 | 465.0 |
| db/db | MSI-1436 | 7.3$^b$ | 36.6 | 8.7$^c$ | 42.8$^a$ | 4.2$^a$ | 20.6$^c$ | 53.5$^c$ |
| db/+ | saline | 10.4 | 53.6 | 3.9 | 19.6 | 4.9 | 25.5 | 94.8 |

P-values (two-sided) are based on comparison of the treated and untreated db/db/groups.
$^a$0.1 < p ≤ 0.05;
$^b$0.001 < p ≤ 0.01;
$^c$p ≤ 0.001.

Example 3

Effect of MSI-1436 and Structural Analogues on Body Weight of CD-1 Mice

Figure 13:
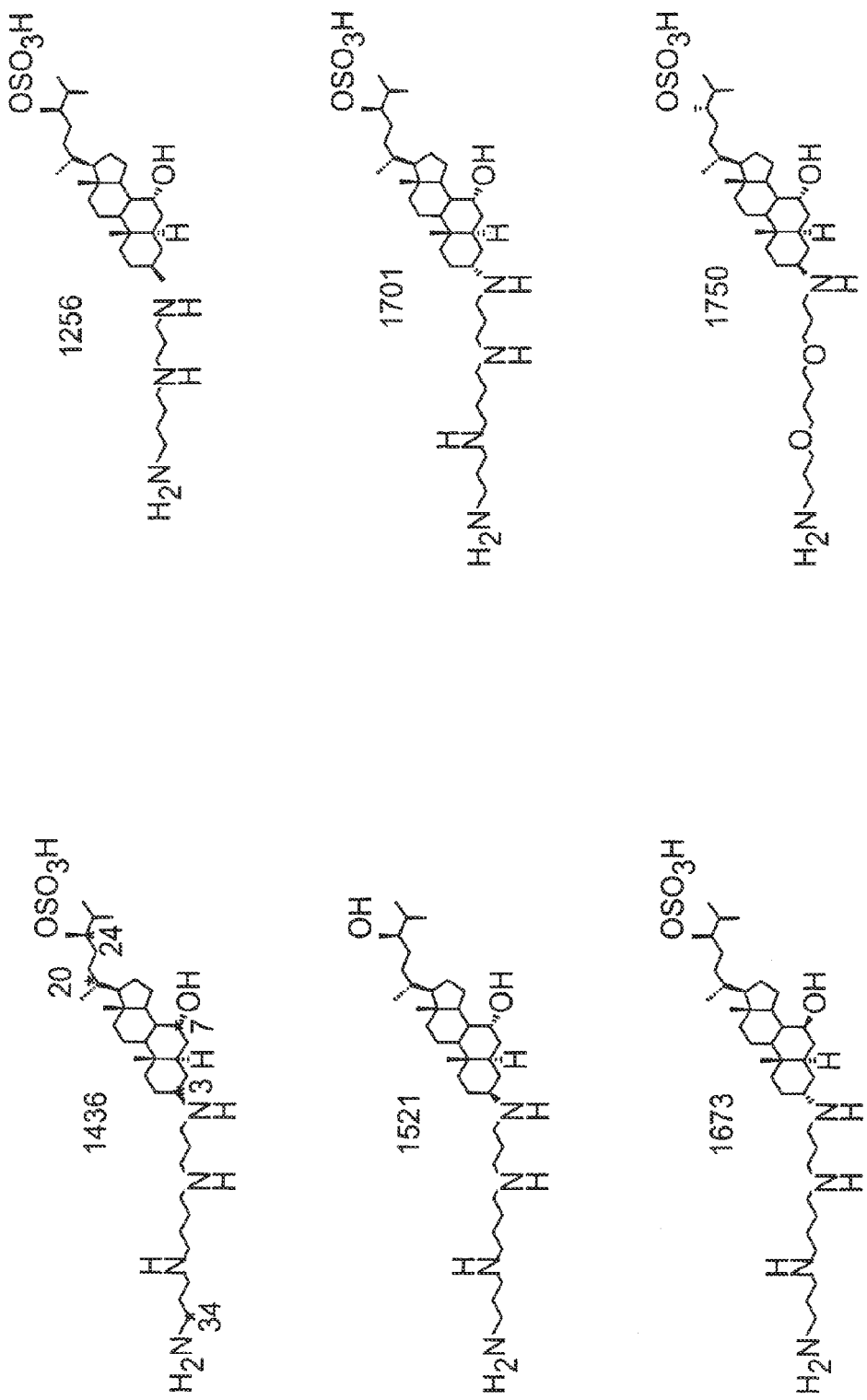
FIG. 13 shows structures of MSI-1436 analogues compared to MSI-1436.
Figure 13:
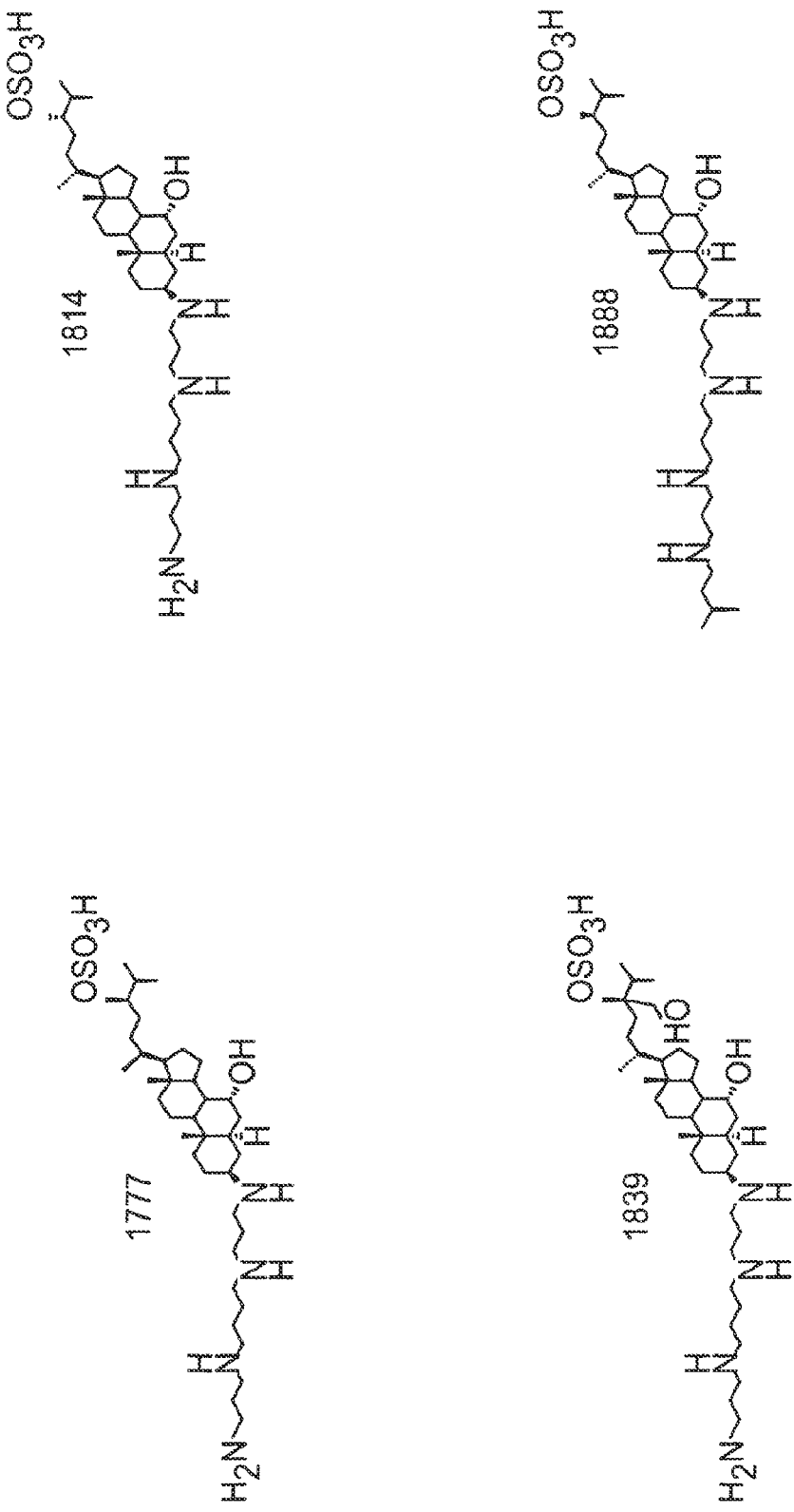
Figure 14:
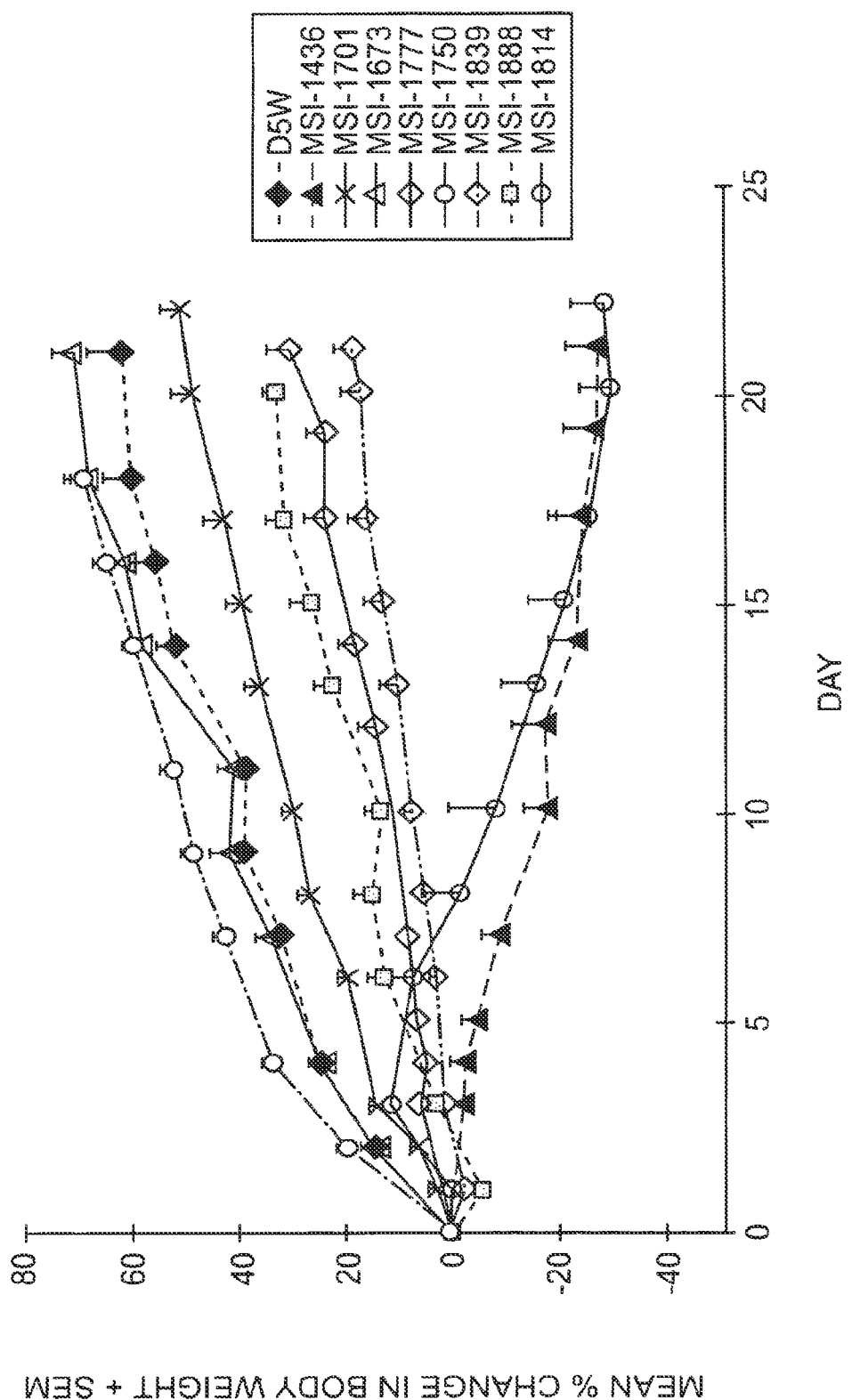
FIG. 14 shows the effect of analogues of MSI-1436 on weight gain in mice.

Experiments were performed using age-matched (4-5 weeks old) male mice (Jackson Laboratories) provided food and water ad lib. Mice corresponding to a single experimental cohort were housed together in a single cage. Animals were used 1 week after arrival. Lights were on from 0600 to 1800 and room temperature was kept at 21±2° C. Daily at 0800-1000 animals were weighed, food and water replaced. Drug dosing was conducted with 10 mg/kg of each compound via the i.p. route every 3 days for 4 doses, beginning on day 0. The structures of the compounds used is shown in FIG. 13 and the results in FIG. 14. Analogues that differ from MSI-1436 at only a single stereocenter, such as MSI-1701 (the polyamine at C-3) or MSI-1777 (the methyl at C-20) exhibit significantly reduced activity, while MSI-1673 (the OH at C-7) is completely inactive. The naturally occurring aminosterol, squalamine, identical to MSI-1436 except for a difference in the polyamine, is inactive highlighting the importance of a precise polyamine structure (not shown). This can be further demonstrated by the analogue MSI-1750, identical to MSI-1436, but differing by the substitution of the two central amino groups of the spermine moiety with oxygens. Additions of longer alkyl groups on the primary amine of the MSI-1436 molecule also reduces activity (MSI-1888), as does the addition of a CH$_2$OH group on C-24 (MSI-1839). The presence of the sulfate on the C-24 hydroxyl moiety is required for activity (MSI-1521) (not shown). However, chirality of the C-24 hydroxyl itself appears to be relatively unimportant (MSI-1814). These studies suggest that MSI-1436 affects weight loss through a specific pathway, rather than as a consequence of a "non-specific' side effect of this chemical class of substance.

Example 4

Extended Dosing of ob/ob Mice with MSI-1436

Male ob/ob mice received weekly dosing of MSI-1436. All doses were administered via the i.p. route (8 animals/dosing level) on Mondays in the A.M. Animals were provided standard mouse chow and water ad lib. Dosing was stopped (FIG. 15A, large circles) or resumed (FIG. 15A, large X) at various times, as noted. Animals in the 20 mg/kg and 10 mg/kg groups were euthanized at days 16 and 30, respectively due to extreme emaciation. Animals being treated weekly at 3.1 mg kg/week stopped receiving MSI-1436 at day 21. MSI-1436 produces a dose dependent reduction in weight gain. Animals receiving 10 or 20 mg/kg/wk lose excessive weight and grow emaciated and moribund within several weeks (FIG. 15 A). However, safely managed weight control (i.e., no deaths) was possible over a four-month period using an intermittent dosing regimen (FIG. 15 A, 3.1 mg/kg/week cohort). When weight fell to about 10% above starting weight, MSI-1436 dosing was stopped, permitting a continued but limited decline in weight; as feeding increased, and weight recovered, dosing resumed.

Following overnight restriction of food, an oral glucose tolerance test was conducted on day 65 on this group, on an untreated group of ob/ob mice, and on a cohort of wt/wt mice of the ob/ob background strain (C57BL/6J) of the same age. Each animal received 5 ml/kg of 30% glucose by gavage. Blood was drawn by tail vein puncture at indicated times and blood glucose measured used a clinical glucose-meter (Life Scan, model One-touch II) (FIG. 15 B). The test revealed a normal metabolic response in the MSI-1436 treated group, in contrast to the diabetic pattern in the vehicle-treated cohort (FIG. 15 B).

Serum cholesterol was measured at study termination. Animals had received their last doses of MSI-1436 one week prior. Blood was drawn after overnight food restriction, and cholesterol measured by automated methodology (Vet-Test model 8008, IDEXX Labs) (FIG. 15 C). It was seen that serum cholesterol was normalized in animals with controlled weight gain (1.0 and 3.1 mg/kg/week) regardless of their absolute weight (FIG. 15 C).

III. Therapeutic Administration and Compositions

The mode of administration of compound 1436 and the other aminosterol compounds may be selected to suit the particular therapeutic use. Also, the compound can be administered to any subject for whom treatment is believed to be beneficial, but administration to humans or other mammals is particularly preferred in the invention. Modes of administration generally include, but are not limited to, transdermal, intramuscular, intraperitoneal, intravenous, subcutaneous, intranasal, inhalation, intralesional, endothelial, and oral routes. The compounds may be administered by any convenient route, for example, by infusion or bolus injection, or by absorption through epithelial or mucocutaneous linings (e.g., oral mucosa, rectal, and intestinal mucosa, etc.), and the active 1436 ingredient may be administered together with other biologically active agents. Administration may be local or systemic.

In this application, the abbreviation "s.q." or "s.c." is used to represent subcutaneous administration of compound 1436 or other substances. The abbreviation "i.p." is used to represent intraperitoneal administration of compound 1436 or other substances. The abbreviation "i.v." is used to represent intravenous administration of compound 1436 or other substances. The abbreviation "i.m." is used to represent intramuscular administration of compound 1436 or other substances. In certain figures attached to this application, one graph axis is labeled "RT." This stands for "reverse transcriptase," which relates to the manner in which a viral enzyme can copy a RNA molecule into a DNA copy. Those skilled in the art are familiar with this measurement technique.

The present invention also provides pharmaceutical compositions that include compound 1436 or another aminosterol compound as an active ingredient. Such pharmaceutical compositions include a therapeutically effective amount of compound 1436 (or a pharmaceutically acceptable salt thereof) or another aminosterol compound (or a pharmaceutically acceptable salt thereof and a pharmaceutically acceptable carrier or excipient. Examples of such a carrier include, but are not limited to, saline, buffered saline, dextrose, water, glycerol, ethanol, and combinations thereof. The particular form and formulation of the pharmaceutical composition should be selected to suit the mode of administration and can be determined and selected by the skilled artisan, e.g., through routine experimentation.

The pharmaceutical composition, if desired, also may contain minor amounts of other conventional agents, such as wetting or emulsifying agents, or pH buffering agents. The pharmaceutical composition may be in any suitable form, such as a liquid solution, suspension, emulsion, tablet, pill, capsule, sustained release formulation, or powder. The pharmaceutical composition also may be formulated as a suppository, with traditional binders and carriers, such as triglycerides. Oral formulations may include standard carriers, such as pharmaceutical grades of mannitol, lactose, starch, magnesium stearate, sodium saccharine, cellulose, magnesium carbonate, etc.

Various delivery systems are known and may be used to administer a therapeutic compound of the invention, e.g., encapsulation in liposomes, microparticles, microcapsules and the like.

In one embodiment, the pharmaceutical composition is formulated in accordance with routine procedures as a pharmaceutical composition adapted for intravenous administration to humans. Typically, compositions for intravenous administration are solutions in sterile isotonic aqueous buffer. Where necessary, the pharmaceutical composition also may include a solubilizing agent and a local anesthetic to ameliorate pain at the site of the injection. Generally, the ingredients are supplied either separately or mixed together in unit dosage form, for example, as a dry lyophilized powder or water-free concentrate in a hermetically sealed container such as an ampule or sachet indicating the quantity of active agent. Where the pharmaceutical composition is to be administered by infusion, it may be dispensed with an infusion bottle containing sterile pharmaceutical grade water or saline. Where the pharmaceutical composition is administered by injection, an ampule of sterile water for injection or saline may be provided so that the ingredients may be mixed prior to administration.

The amount of the therapeutic compound of the invention that will be effective in the treatment of a particular disorder or condition will depend on the nature of the disorder or condition, and this amount can be determined by standard clinical techniques known to those skilled in the art through routine experimentation. The precise dose to be employed in the pharmaceutical composition also will depend on the route of administration and the seriousness of the disease or disorder, and should be decided according to the judgment of the practitioner and each patient's circumstances. Effective therapeutical doses may be determined from extrapolations of dose-response curves derived from in vitro or animal-model test systems.

The following dosage ranges are exemplary. Suitable dosages for intravenous administration are generally about 20 micrograms to 40 milligrams of active compound per kilogram body weight. Suitable dosage ranges for intranasal administration are generally about 0.01 mg/kg body weight to 1 mg/kg body weight. Suitable dosage ranges for topical administration are generally at least about 0.01% by weight. Suitable dosages for oral administration are generally about 500 micrograms to 800 milligrams per kilogram body weight, and preferably about 1-200 mg/kg body weight. Suppositories generally contain, as the active ingredient, 0.5 to 10% by weight of the aminosterol active ingredient. Oral formulations preferably contain 10% to 95% active ingredient.

Exemplary dosages of the aminosterol active ingredient for most pharmacological or therapeutic uses fall within the range of about 0.01 mg kg body weight to about 100 mg/kg body weight. Preferred dosages are from 0.1 to 25 mg/kg body weight.

For subcutaneous administration, applicants have performed a pharmacokinetics study of the administration of compound 1436 in a mouse model. For this test, compound 1436 was administered s.q. at a dose of 10 mg/kg in mice. The peak 1436 concentration in the blood plasma from this 10 mg/kg dose was about 175 µg/ml after a time of about 2 hours. After 48 hours, the 1436 concentration is still about 10-15 µg/ml. This data indicates that relatively small 1436 doses may be used for s.q. administration. This data also provides an indication that oral dosing of 1436 will be effective.

The invention also may include a pharmaceutical pack or kit including one or more containers filled with pharmaceutical compositions in accordance with the invention. Associated with such containers may be a notice in the form prescribed by a government agency regulating the manufacture, use or sale of pharmaceuticals or biological products, which notice reflects approval by the agency of manufacture, use or sale for human administration.

By the term "effective amount" in this application, applicants refer to a suitable amount of the active ingredient of the invention, with an appropriate carrier or excipient, including a sufficient amount of the active ingredient to provide the desired effects or results. The effective amount can be readily ascertained by those skilled in the art through routine experimentation.

In describing the invention, applicant has stated certain theories in an effort to disclose how and why the invention works in the manner in which it works. These theories are set forth for informational purposes only. Applicants do not wish to be bound by any specific theory of operation.

While the invention has been described in terms of various specific preferred embodiments and specific examples, those skilled in the art will recognize that various changes and modifications can be made without departing from the spirit and scope of the invention, as defined in the appended claims.

We claim:
1. The compound
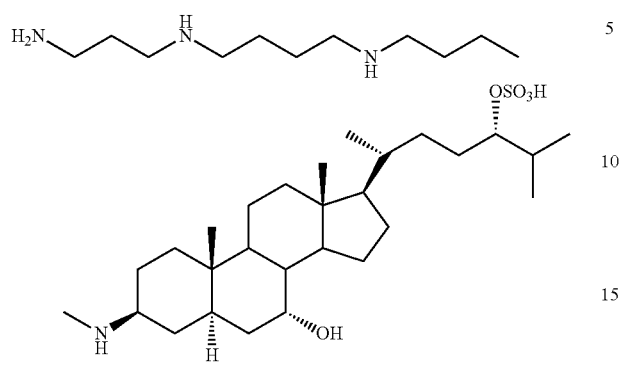
or a pharmaceutically acceptable salt thereof.
2. A pharmaceutical composition comprising the compound of claim 1 or a pharmaceutically acceptable salt thereof and a pharmaceutically acceptable carrier or excipient.
* * * * *